(12) United States Patent
Tamao et al.

(10) Patent No.: US 6,465,594 B1
(45) Date of Patent: Oct. 15, 2002

(54) PHOSPHINE DERIVATIVE AND POLYMER THEREOF AND TRANSITION METAL COMPLEX COMPRISING THE SAME

(75) Inventors: Kyoko Tamao, Kyoto; Noboru Sayo, Kanagawa, both of (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 09/539,413

(22) Filed: Mar. 30, 2000

(30) Foreign Application Priority Data

Mar. 30, 1999 (JP) .......................................... 11-088601

(51) Int. Cl.[7] .................................................. C08F 30/02
(52) U.S. Cl. ........................ 526/274; 526/240; 526/347; 526/340
(58) Field of Search ................................ 526/240, 274, 526/347, 340

(56) References Cited

U.S. PATENT DOCUMENTS

| 3,847,997 A | | 11/1974 | Allen | |
| 4,506,030 A | * | 3/1985 | Jones | 502/155 |
| 6,162,951 A | * | 12/2000 | Polywka et al. | 568/13 |

FOREIGN PATENT DOCUMENTS

| EP | 0 135 392 A2 | 3/1985 | |
| EP | 0 864 577 A2 | 9/1998 | ......... C07F/9/6574 |
| EP | 0 877 029 A2 | 11/1998 | ......... C07F/9/6574 |
| EP | 0 877 029 | * 11/1998 | |
| WO | 98/12202 | 3/1998 | ......... C07F/9/50 |

OTHER PUBLICATIONS

Fujii et al., Tetrahedron Letters 40, 8011–8014 (1999).*
Bayston et al., J. Org. Chem., 63, 3137–3140 (1998).*
Chemical Abstracts, vol. 113, No. 12, Sep. 17, 1990: Columbus, Ohio, US; abstract No. 98270, p. 18 XP002107088 & JP 02 049009 A (Tokuyama Soda Co.) Feb. 19, 1990.

* cited by examiner

Primary Examiner—David W. Wu
Assistant Examiner—Ling-Siu Choi
(74) Attorney, Agent, or Firm—Sughrue Mion, PLLC

(57) ABSTRACT

Disclosed are a phosphine derivative represented by formula (I):

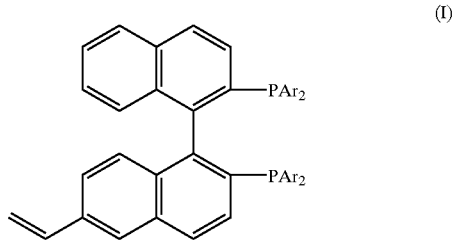

(I)

wherein Ar represents a substituted or unsubstituted phenyl group or a substituted or unsubstituted naphthyl group, a transition metal complex comprising the phosphine derivative or a polymer thereof as a ligand, and a process for producing an optically active amino acid compound by asymmetric hydrogenation using the transition metal complex as a catalyst.

9 Claims, No Drawings

PHOSPHINE DERIVATIVE AND POLYMER THEREOF AND TRANSITION METAL COMPLEX COMPRISING THE SAME

FIELD OF THE INVENTION

This invention relates to a phosphine derivative, a polymer comprising the phosphine derivative, a transition metal complex comprising the phosphine derivative or a polymer thereof, and a process for producing an optically active compound by asymmetric hydrogenation using the transition metal complex as a catalyst.

BACKGROUND OF THE INVENTION

A large number of transition metal complexes have been used in catalyst systems for organic syntheses. In particular, noble metal complexes, though expensive, have enjoyed wide use for their stability and ease of handling. Extensive study has been given to use of transition metal complexes, such as nobel metal complexes, as a catalyst in various syntheses, and we can find many reports on the transition metal complexes which have effected organic synthesis reactions, inclusive of asymmetric reactions, that had been regarded as impossible with traditional means.

Optically active ligands useful in asymmetric catalytic reactions include various types. Taking note of asymmetric hydrogenation using a transition metal-phosphine complex, 2,2'-bis(diphenylphosphino)-1,1'-binaphthalene (hereinafter referred to as BINAP) is among the optically active ligands having the most excellent ability of asymmetric recognition. There are many reports on hydrogenation reaction of olefins or ketone compounds using a Rh or Ru complex comprising BINAP as a ligand (see, for example, Ryoji Noyori, *Asymmetric Catalysis in Organic Synthesis*, pp. 16–85, A Wiley-Interscience Publication (1994)).

However, these expensive noble metal catalysts cannot be recovered, or their recovery requires complicated operation involving a heavy loss. In addition, it is impossible or uneconomical to reuse the recovered catalyst. It has therefore been demanded to develop a catalyst which can easily be separated and reused and maintains its activity and selectivity even in repeated use.

Application of synthetic chiral polymers as a medium for resolution of a racemate, a reagent or a catalyst for asymmetric synthesis, and the like has been studied extensively. Studies on the ability of chiral polymers in asymmetric recognition have recently made remarkable advances. In particular, when applied to stereoselective organic reactions, chiral polymers provide a specific reaction site different from general homogeneous reaction systems. Use of a polymeric reagent or a polymeric catalyst in organic synthesis is advantageous for improving industrial processes in that the product can be separated easily and that the reagent or catalyst can be reused.

Applications of the chiral polymers to stereoselective organic syntheses include the following examples.

1) An optically active amino acid is allowed to react with 4-vinylbenzenesulfonyl chloride to obtain a chiral monomer (C), which is copolymerized with styrene and divinylbenzene to obtain a polymer having the following structural units:

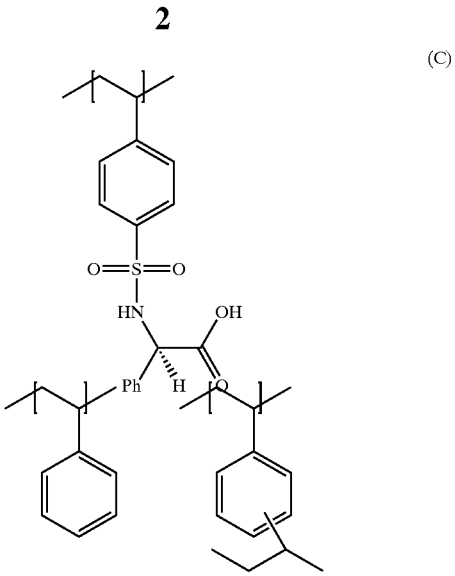
(C)

The resulting polymer ligand and diborane are allowed to react with each other to prepare chiral polymer-bound oxabororidinonone, which is used as a Lewis acid catalyst for Diels-Alder reaction between cyclopentadiene and metacrolein (S. Itsuno, et al., *Tetrahedron: Asymmetry*, vol. 6, p. 2547 (1995)).

2) A polymer of a manganese-salen complex (D) is used in asymmetric epoxidation of olefins (S. Sivaram, et al., *Tetrahedron: Asymmetry*, vol. 6, p. 2105 (1995)).

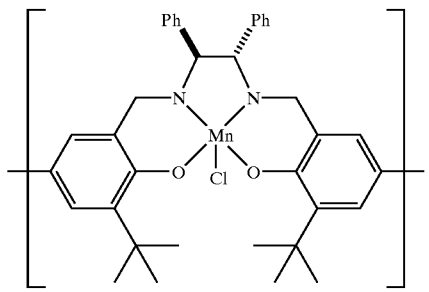
(D)

3) 2-p-Styryl-4,5-bis[(dibenzophosphoryl)methyl]-1,3-dioxolane (E), styrene, and divinylbenzene are copolymerized to obtain a chiral polymer having the following structural units:

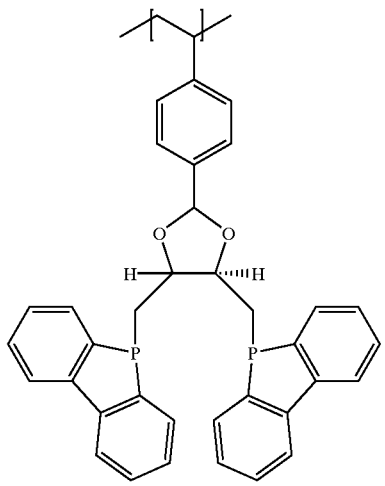
(E)

-continued

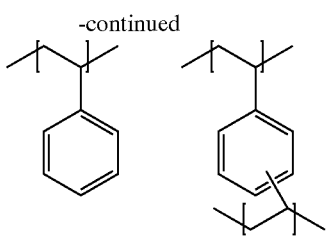

Platinum chloride is coordinated to the resulting polymer ligand to obtain a chiral polymer catalyst. Styrene is hydroformylated by using the resulting polymer catalyst in the copresence of tin chloride (J. K. Stille, et al., *J. Org. Chem.*, vol. 51, p. 4189 (1986)).

However, any of these known polymeric catalysts has not been put to practical use due to insufficient catalytic activity or a lower reaction yield than reached by using the corresponding monomer.

SUMMARY OF THE INVENTION

An object of the present invention is to provide a polymer-bearing ligand making a catalyst for asymmetric synthesis reactions which exhibits satisfactory performance in catalytic activity, optical purity, and the like.

The present inventors synthesized a monomer having a binaphthyl skeleton with a diarylphosphino group at the 2,2'-positions and a vinyl group at the 6-position and prepared a copolymer comprising the monomer, a styrene derivative, and divinylbenzene. They have found the resulting polymer excellent as a ligand of a catalyst for asymmetric hydrogenation reaction.

The invention provides a phosphine derivative represented by formula (I):

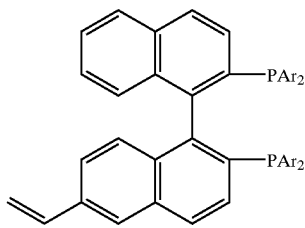

(I)

wherein Ar represents a substituted or unsubstituted phenyl group or a substituted or unsubstituted naphthyl group.

The invention also provides an oligomer or polymer comprising a structural unit represented by formula (III):

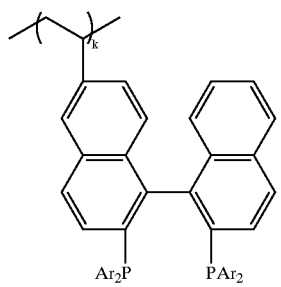

(III)

wherein Ar is as defined above; and k represents an integer of 2 to 100.

The invention further provides a transition metal complex obtained by allowing a transition metal compound to react on the compound represented by formula (I) or the oligomer or polymer having the structural unit of formula (III).

The invention furthermore provides a process for producing an optically active amino acid compound represented by formula (B):

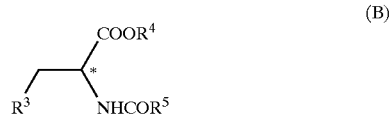

(B)

wherein $R^3$ represents a substituted or unsubstituted alkyl group or a substituted or unsubstituted aryl group; $R^4$ represents a hydrogen atom, an alkyl group, a substituted or unsubstituted aryl group or a substituted or unsubstituted aralkyl group; $R^5$ represents a hydrogen atom, an alkyl group, an alkoxy group, a substituted or unsubstituted aryl group or a substituted or unsubstituted aralkyloxy group; and * indicates an asymmetric carbon atom, which comprises asymmetrically hydrogenating a dehydroamino acid compound represented by formula (A):

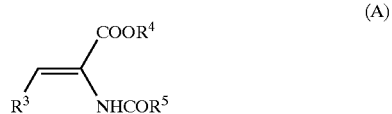

(A)

wherein $R^3$, $R^4$, and $R^5$ are as defined above, in the presence of the above-described transition metal complex.

DETAILED DESCRIPTION OF THE INVENTION

In formula (I), Ar represents a substituted or unsubstituted phenyl group or a substituted or unsubstituted naphthyl group. The substituents that may be on the phenyl or naphthyl group include a lower alkyl group having 1 to 4 carbon atoms, such as methyl, ethyl, propyl, isopropyl, n-butyl, t-butyl or isobutyl; a halogen atom, such as fluorine, chlorine or bromine; a lower alkoxy group, such as methoxy, ethoxy, propoxy or butoxy; a halogenated lower alkyl group, such as trifluoromethyl or trichloromethyl; and a benzyloxy group. Ar preferably represents phenyl, 4-tolyl, 4-methoxyphenyl, 3,5-xylyl, and naphthyl groups.

The compound (I) of the invention can be prepared through, for example, the following reaction scheme, in which a phenyl group is taken as an example of Ar:

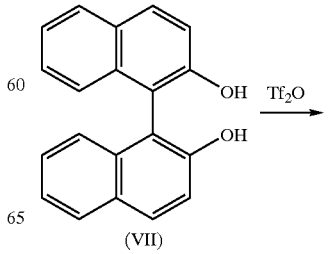

(VII)

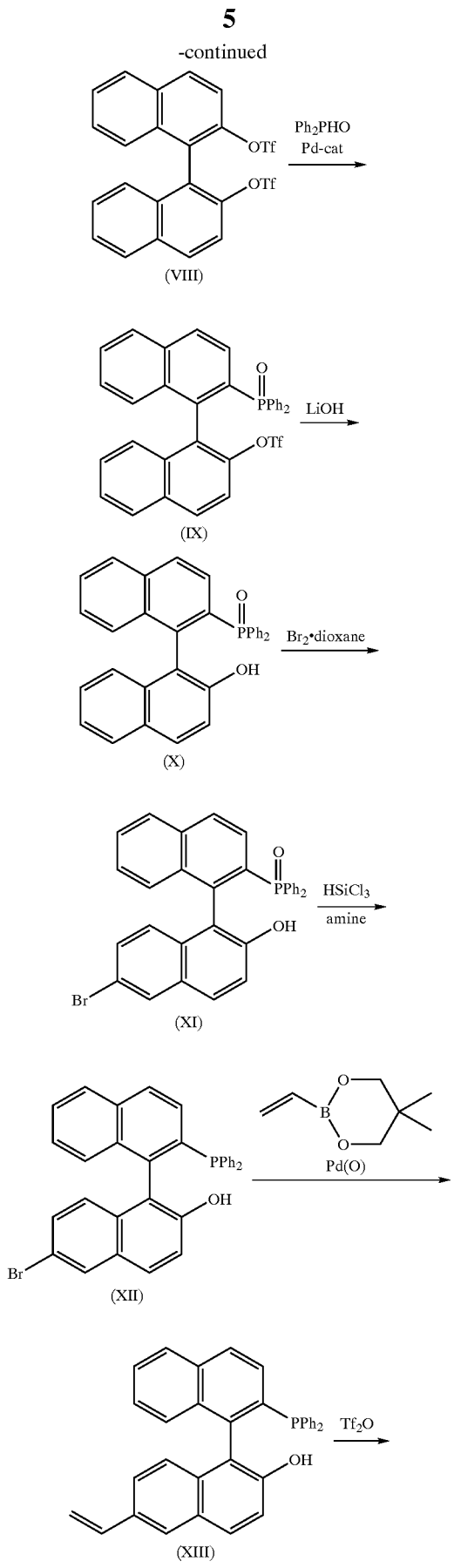

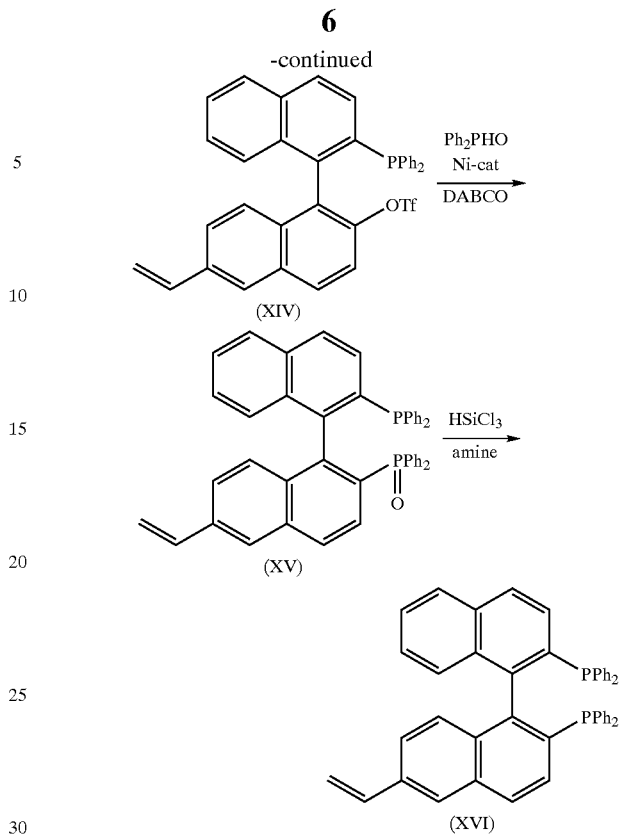

Optically active binaphthol (VII) and trifluoromethanesulfonic acid anhydride (Tf₂O) are allowed to react in methylene chloride in the presence of pyridine to obtain 2,2'-bis(trifluoromethanesulfonyloxy)-1,1'-binaphthalene (VIII) in accordance with the method taught in the literature (M. Vondenhof and J. Mattay, *Tetrahedron Lett.*, vol. 31, pp. 985–988 (1990), L. Kurz, et al., *Tetrahedron Lett.*, vol. 31, pp. 6321–6324 (1990), and Y. Uozumi, et al., *J. Org. Chem.*, vol. 58, pp. 1945–1948 (1993)). The compound (VIII) is allowed to react with diphenylphosphine oxide (Ph₂PHO) in the presence of a catalytic amount of a palladium-phosphine complex to obtain 2'-diphenylphosphinyl-2-trifluoromethanesulfonyloxy-1,1'-binaphthalene (IX), which is then hydrolyzed with lithium hydroxide (LiOH) to form 2'-diphenylphosphinyl-2-hydroxy-1,1'-binaphthalene (X). The compound (X) is brominated in dioxane to give 2'-diphenylphosphinyl-2-hydroxy-6-bromo-1,1'-binaphthalene (XI). The compound (XI) is reduced with trichlorosilane (HSiCl₃) in the presence of an amine to obtain 2'-diphenylphosphino-2-hydroxy-6-bromo-1,1'-binaphthalene (XII). The compound (XII) is allowed to react with 2-vinyl-5,5-dimethyl-1,3,2-dioxaborinane in the presence of a palladium catalyst to obtain 6-vinyl-2'-diphenylphosphino-2-hydroxy-1,1'-binaphthalene (XIII) in accordance with the method described in the literature (Y. Miyaura and A. Suzuki, *J.C.S. Chem. Commun.*, p. 866 (1979)). The compound (XIII), trifluoromethanesulfonic acid anhydride (Tf₂O), and sodium hydride are made to react to obtain 6-vinyl-2'-diphenylphosphino-2-trifluoromethanesulfonyloxy-1,1'-binaphthalene (XIV). The compound (XIV) is allowed to react with diphenylphosphine oxide (Ph₂PHO) in the presence of a nickel-phosphine complex and 1,4-diazabicyclo[2,2,2]octane (DABCO) to afford 6-vinyl-2'-diphenylphosphino-2-diphenylphosphinyl-1,1'-binaphthalene (XV), which is reduced with trichlorosilane (HSiCl₃) in the presence of an amine to yield 6-vinyl-2,2'-bis(diphenylphosphino)-1,1'-binaphthalene (XVI) as a final product.

The above-described process also applies to the production of the compounds (I) in which Ar is other than a phenyl group.

The compound (I) coordinates to a transition metal as a ligand to form a transition metal complex. Of transition metal complexes obtainable preferred are those represented by formula (II):

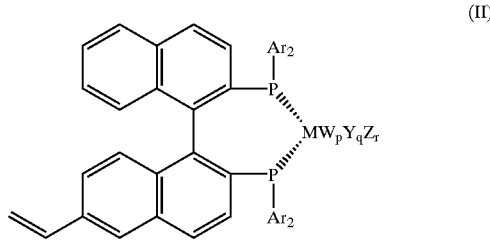

(II)

wherein Ar is as defined above; M represents ruthenium, rhodium, iridium or palladium; W represents an allyl group, a methallyl group, 1,5-cyclooctadiene, norbornadiene, a halogen atom, an acetoxy group or an acetylacetonato group; Y represents a hydrogen atom, a halogen atom, $ClO_4$, $BF_4$, $PF_6$, $BPh_4$ (tetraphenylborate), OTf (trifluoromethanesulfonyloxy) or $SbF_6$; Z represents a substituted or unsubstituted benzene; p, q, and r each represent a number of 0 to 2 provided that p, q, and r do not simultaneously represent 0.

In formula (II), substituents which may be on benzene as Z include a lower alkyl group, a halogen atom, a lower alkoxy group, a halogenated lower alkyl group, and a benzyloxy group. Examples of the lower alkyl group, halogen atom, lower alkoxy group and halogenated lower alkyl group include those listed above as the substituents of Ar.

Specific examples of the transition metal complexes according to the invention are shown below. In the formulae given hereunder, cod stands for 1,5-cyclooctadiene; nbd, norbornadiene; Ph, phenyl; Ac, acetyl; OAc, acetoxy; acac, acetylacetonato; and OTf, trifluoromethanesulfonyloxy, respectively. "L" stands for a ligand of formula (I) and is intended to specifically means (R)-6-vinyl-2,2'-bis(diphenylphosphino)-1,1'-binaphthalene as a typical example.

Rhodium Complexes:

Rhodium compounds used as a complex precursor for forming rhodium complexes include $RhCl_3$, $RhBr_3$, $RhI_3$, $[Rh(cod)Cl]_2$, $[Rh(cod)Br]_2$, $[Rh(cod)I]_2$, $[Rh(nbd)Cl]_2$, $[Rh(nbd)Br]_2$, $[Rh(nbd)I]_2$, $[Rh(cod)(OAc)]_2$, $[Rh(nbd)(OAc)]_2$, $Rh(cod)(acac)$, $Rh(nbd)(acac)$, $Rh(CO)_2(acac)$, $[Rh(CO)_2Cl]_2$, $[Rh(CO)_2Br]_2$, $[Rh(CO)_2I]_2$, $[Rh(cod)_2]BF_4$, $[Rh(cod)_2]ClO_4$, $[Rh(cod)_2]PF_6$, $[Rh(cod)_2]BPh_4$, $[Rh(nbd)_2]BF_4$, $[Rh(nbd)_2]ClO_4$, $[Rh(nbd)_2]PF_6$, $[Rh(nbd)_2]BPh_4$, $[Rh(cod)_2]OTf$, $[Rh(cod)_2]SbF_6$, $[Rh(nbd)_2]OTf$, and $[Rh(nbd)_2]SbF_6$.

The method described in the literature (R. R. Schrock and J. A. Osborn, J. Am. Chem. Soc., vol. 93, p. 2397 (1971)) can be followed to prepare the rhodium complexes. For example, bis(1,5-cyclooctadiene)rhodium hexafluorophosphate ($[Rh(cod)_2]PF_6$) and L are made to react with each other. Specific examples of the rhodium complexes thus obtained are Rh(acac)(L), Rh(cod)Cl(L), Rh(nbd)Cl(L), $[Rh(cod)(L)]ClO_4$, $[Rh(cod)(L)]BF_4$, $[Rh(cod)(L)]PF_6$, $[Rh(nbd)(L)]ClO_4$, $[Rh(nbd)(L)]BF_4$, and $[Rh(nbd)(L)]PF_6$.

Ruthenium Complexes:

Ruthenium compounds useful as a complex precursor include $[RuCl_2(benzene)]_2$, $[RuBr_2(benzene)]_2$, $[RuI_2(benzene)]_2$, $[RuCl_2(p-cymene)]_2$, $[RuBr_2(p-cymene)]_2$, $[RuI_2(p-cymene)]_2$, $[RuCl_2(mesitylene)]_2$, $[RuBr_2(mesitylene)]_2$, $[RuI_2(mesitylene)]_2$, $[RuCl_2(hexamethylbenzene)]_2$, $[RuBr_2(hexamethylbenzene)]_2$, $[RuI_2(hexamethylbenzene)]_2$, $[(π-allyl)Ru(cod)]_2$, $[(π-allyl)Ru(nbd)]_2$, $[(π-methallyl)Ru(cod)]_2$, and $[(π-methallyl)Ru(nbd)]_2$.

The ruthenium complexes are prepared by, for example, heating bis[ruthenium(p-cymene)iodide]($[RuI_2(p-cymene)]_2$) and L in methylene chloride with stirring under heat as taught in the literature (K. Mashima, et al., J. Chem. Soc., Chem. Commun., p. 1208 (1989)). Specific examples of the ruthenium complexes are [RuCl(benzene)(L)]Cl, [RuBr(benzene)(L)]Br, [RuI (benzene)(L)]I, [RuCl(p-cymene)(L)]Cl, [RuBr(p-cymene)(L)]Br, [RuI(p-cymene)(L)]I, [RuCl(mesitylene)(L)]Cl, [RuBr(mesitylene)(L)]Br, [RuI (mesitylene)(L)]I, [RuCl(hexamethylbenzene)(L)]Cl, [RuBr(hexamethylbenzene)(L)]Br, and [RuI(hexamethylbenzene)(L)]I.

Palladium Complexes:

Palladium compounds which can be used as a palladium complex precursor include $PdCl_2$, $PdBr_2$, $PdI_2$, $[(π-allyl)PdCl]_2$, $[(π-allyl)PdBr]_2$, $[(π-allyl)PdI]_2$, $[(p-methallyl)PdCl]_2$, $[(π-methallyl)PdBr]_2$, $[(π-methallyl)PdI]_2$, $PdCl_2(CH_3CN)_2$, $PdBr_2(CH_3CN)_2$, $PdI_2(CH_3CN)_2$, $PdCl_2(C_6H_5CN)_2$, $PdBr_2(C_6H_5CN)_2$, $PdI_2(C_6H_5CN)_2$, $PdCl_2(cod)$, $PdBr_2(cod)$, $PdI_2(cod)$, $PdCl_2(nbd)$, $PdBr_2(nbd)$, $PdI_2(nbd)$, $Pd(OAc)_2$, and $Pd(acac)_2$.

Palladium complexes are prepared by, for example, allowing L and π-allylpalladium chloride ($[(π-allyl)PdCl]_2$) to react in accordance with the method disclosed in the literature (Y. Uozumi and T. Hayashi, J. Am. Chem. Soc., vol. 113, p. 9887 (1991)). Specific examples of the palladium complexes are $PdCl_2(L)$, $(π-allyl)Pd(L)$, $[Pd(L)]ClO_4$, $[Pd(L)]PF_6$, and $[Pd(L)]BF_4$.

Iridium Complexes:

Iridium compounds used as an iridium complex precursor include $IrCl_3$, $IrBr_3$, $IrI_3$, $[Ir(cod)Cl]_2$, $[Ir(cod)Br]_2$, $[Ir(cod)I]_2$, $[Ir(nbd)Cl]_2$, $[Ir(nbd)Br]_2$, $[Ir(nbd)I]_2$, $[Ir(cod)(OAc)]_2$, $[Ir(nbd)(OAc)]_2$, Ir(cod)(acac), Ir(nbd)(acac), $Ir(CO)_2(acac)$, $[Ir(CO)_2Cl]_2$, $[Ir(CO)_2Br]_2$, $[Ir(CO)_2I]_2$, $[Ir(cod)_2]BF_4$, $[Ir(cod)_2]ClO_4$, $[Ir(cod)_2]PF_6$, $[Ir(cod)_2]BPh_4$, $[Ir(nbd)_2]BF_4$, $[Ir(nbd)_2]ClO_4$, $[Ir(nbd)_2]PF_6$, and $[Ir(nbd)_2]BPh_4$.

The iridium complexes are prepared by, for example, stirring L and [(1,5-cyclooctadiene)(acetonitrile)iridium] tetrafluoroborate ($[Ir(cod)(CH_3CN)_2]BF_4$) in tetrahydrofuran in accordance with the method disclosed in the literature (K. Mashima, et al., J. Organomet. Chem., vol. 428, p. 213 (1992)). Specific examples of the iridium complexes include $[Ir(cod)(L)]ClO_4$, $[Ir(cod)(L)]PF_6$, $[Ir(cod)(L)]BF_4$, $[Ir(nbd)(L)]ClO_4$, $[Ir(nbd)(L)]PF_6$, $[Ir(nbd)(L)]BF_4$, Ir(cod)(L)Cl, Ir(nbd)(L)Cl, Ir(cod)(L)Br, and Ir(nbd)(L)Br.

The oligomer or polymer according to the invention comprises a structural unit represented by formula (III):

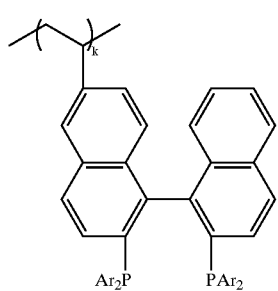

(III)

wherein Ar and k are as defined above.

The polymer preferably includes a copolymer comprising the structural unit represented by formula (III) and a structural unit represented by formula (IV) and/or a structural unit represented by formula (V):

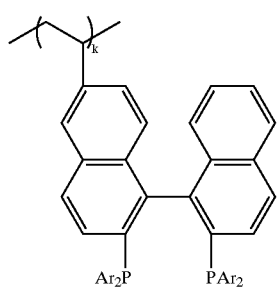

(III)

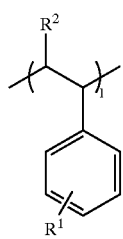

(IV)

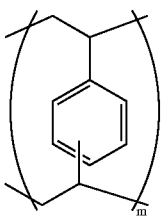

(V)

wherein Ar and k are as defined above; $R^1$ represents a hydrogen atom, a lower alkyl group, a lower alkoxy group or a halogen atom; $R^2$ represents a hydrogen atom or a methyl group; l and m each represent an integer of 0 to 1000 provided that l and m do not simultaneously represent 0 and that (k+l+m) ranges 10 to 1000.

In formula (IV), $R^1$ includes a hydrogen atom, a lower alkyl group having 1 to 4 carbon atoms, such as methyl, ethyl, isopropyl, n-butyl, and t-butyl, a lower alkoxy group having 1 to 4 carbon atoms, such as methoxy, ethoxy, propoxy and butoxy, and a halogen atom, such as fluorine, chlorine, and bromine.

The oligomer or polymer comprising the unit (III) is obtained by polymerizing the phosphine derivative of formula (I). The polymer comprising the units (III) and (IV) and/or (V) is obtained by copolymerizing the phosphine derivative (I) and a styrene derivative represented by formula (IVa):

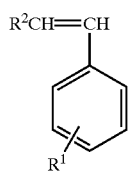

(IVa)

wherein $R^1$ and $R^2$ are as defined above, and/or divinylbenzene represented by formula (Va):

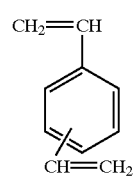

(Va)

The polymerization reaction is carried out by solution polymerization, suspension polymerization and the like. For example, a solution or suspension of the monomer(s) in a solvent, such as a polyvinyl alcohol aqueous solution, a halogenated hydrocarbon (e.g., chloroform) or a hydrocarbon (e.g., toluene), is charged in a reaction vessel in an inert atmosphere (e.g., nitrogen or argon). An azo compound (e.g., 2,2'-azobis(2,4-dimethylvaleronitrile) or azobisisobutyronitrile) or a peroxide is added as a radical polymerization initiator, and the mixture was allowed to react at 60 to 100° C. under atmospheric pressure for 1 hour to 2 days.

The copolymerization ratio of the units (III), (IV), and (V), represented by the molar ratio k:l:m, is 2 to 100:0 to 1000:0 to 1000, preferably 2 to 100:100 to 1000:0 to 1000. The degrees of polymerization of the units (III), (IV), and (V) are represented by k, l, and m, respectively, and (k+l+m) is in the range of from 10 to 1000.

The oligomer or polymer having the structural unit (III) and the polymer having the structural units (III) and (IV) and/or (V) act as a ligand coordinating to a transition metal to form transitionmetal complexes. The transition metal complexes formed include those having a structural unit represented by formula (VI):

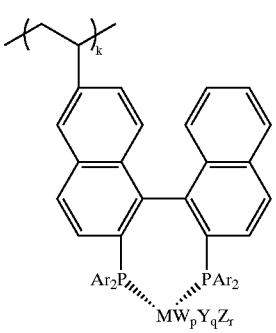

(VI)

wherein Ar, M, W, Y, Z, p, q, r, and k are as defined above, and those comprising the following structural units (VI), (IV) and (V):

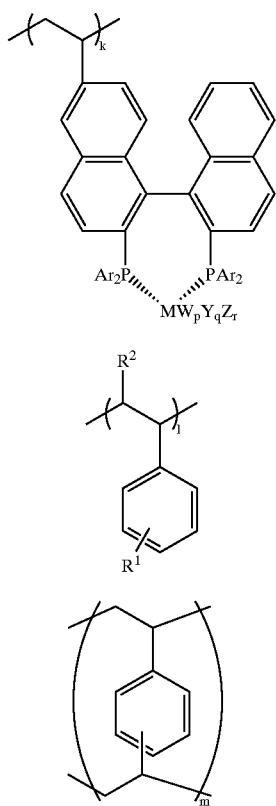

wherein Ar, R¹, R², M, W, Y, Z, p, q, r, k, l, and m are as defined above.

Examples of the oligomeric or polymeric complexes are described below. In the formulae given hereunder, cod, nbd, Ph, Ac, OAc, acac, and OTf have the same meanings as defined above. "L" stands for a ligand of formula (III) and is specifically intended to mean a structural unit derived from 6-vinyl-2,2'-bis(diarylphosphino)-1,1'-binaphthalene. k, the degree of polymerization, is as defined above (an integer of 2 to 100). In these examples the polymer having the unit (III) can be replaced with the polymer having the units (III), (IV), and (V).

Rhodium Complexes:

Rhodium compounds used as a rhodium complex precursor include $RhCl_3$, $RhBr_3$, $RhI_3$, $[Rh(cod)Cl]_2$, $[Rh(cod)Br]_2$, $[Rh(cod)I]_2$, $[Rh(nbd)Cl]_2$, $[Rh(nbd)Br]_2$, $[Rh(nbd)I]_2$, $[Rh(cod)(OAc)]_2$, $[Rh(nbd)(OAc)]_2$, $Rh(cod)(acac)$, $Rh(nbd)(acac)$, $Rh(CO)_2(acac)$, $[Rh(CO)_2Cl]_2$, $[Rh(CO)_2Br]_2$, $[Rh(CO)_2I]_2$, $[Rh(cod)_2]BF_4$, $[Rh(cod)_2]ClO_4$, $[Rh(cod)_2]PF_6$, $[Rh(cod)_2]BPh_4$, $[Rh(nbd)_2]BF_4$, $[Rh(nbd)_2]ClO_4$, $[Rh(nbd)_2]PF_6$, $[Rh(nbd)_2]BPh_4$, $[Rh(cod)_2]OTf$, $[Rh(cod)_2]SbF_6$, $[Rh(nbd)_2]OTf$, and $[Rh(nbd)_2]SbF_6$.

The method described in the literature (R. R. Schrock and J. A. Osborn, J. Am. Chem. Soc., vol. 93, p. 2397 (1971)) can be followed to prepare the rhodium complexes. For example, bis(1,5-cyclooctadiene)rhodium hexafluorophosphate ($[Rh(cod)_2]PF_6$) and L are made to-react with each other. Specific examples of the oligomeric or polymeric rhodium complexes thus obtained are $Rh(acac)_k(L)$, $[Rh(cod)Cl]_k(L)$, $[Rh(nbd)Cl]_k(L)$, $[Rh_k(cod)_k(L)](ClO_4)_k$, $[Rh_k(cod)_k(L)](BF_4)_k$, $[Rh_k(cod)_k(L)](PF_6)_k$, $[Rh_k(nbd)_k(L)](ClO_4)_k$, $[Rh_k(nbd)_k(L)](BF_4)_k$, and $[Rh_k(nbd)_k(L)](PF_6)_k$.

Ruthenium Complexes:

Ruthenium compounds useful as a complex precursor include $[RuCl_2(benzene)]_2$, $[RuBr_2(benzene)]_2$, $[Ru_2(benzene)]_2$, $[RuCl_2(p\text{-cymene})]_2$, $[RuBr_2(p\text{-cymene})]_2$, $[RuI_2(p\text{-cymene})]_2$, $[RuCl_2(mesitylene)]_2$, $[RuBr_2(mesitylene)]_2$, $[RuI_2(mesitylene)]_2$, $[RuCl_2(hexamethylbenzene)]_2$, $[RuBr_2(hexamethylbenzene)]_2$, $[RuI_2(hexamethylbenzene)]_2$, $[(\pi\text{-allyl})Ru(cod)]_2$, $[(\pi\text{-allyl})Ru(nbd)]_2$, $[(\pi\text{-methallyl})Ru(cod)]_2$, and $[(\pi\text{-methallyl})Ru(nbd)]_2$.

The ruthenium complexes are prepared by, for example, heating bis[ruthenium(p-cymene)iodide]($[RuI_2(p\text{-cymene})]_2$) and L in methylene chloride with stirring as taught in the literature (K. Mashima, et al., J. Chem. Soc., Chem. Commun., p. 1208 (1989)). Specific examples of the oligomeric or polymeric ruthenium complexes are $[Ru_kCl_k(benzene)_k(L)]Cl_k$, $[Ru_kBr_k(benzene)_k(L)]Br_k$, $[Ru_kI_k(benzene)_k(L)]I_k$, $[Ru_kCl_k(p\text{-cymene})_k(L)]Cl_k$, $[Ru_kBr_k(p\text{-cymene})_k(L)]Br_k$, $[Ru_kI_k(p\text{-cymene})_k(L)]I_k$, $[Ru_kCl_k(mesitylene)_k(L)]Cl_k$, $[Ru_kBr_k(mesitylene)_k(L)]Br_k$, $[Ru_kI_k(mesitylene)_k(L)]I_k$, $[Ru_kCl_k(hexamethylbenzene)_k(L)]Cl_k$, $[Ru_kBr_k(hexamethylbenzene)_k(L)]B_k$, and $[Ru_kI_k(hexamethylbenzene)_k(L)]I_k$.

Palladium Complexes:

Palladium compounds which can be used as a palladium complex precursor include $PdCl_2$, $PdBr_2$, $PdI_2$, $[(\pi\text{-allyl})PdCl]_2$, $[(\pi\text{-allyl})PdBr]_2$, $[(\pi\text{-allyl})PdI]_2$, $[(\pi\text{-methallyl})PdCl]_2$, $[(\pi\text{-methallyl})PdBr]_2$, $[(\pi\text{-methallyl})PdI]_2$, $PdCl_2(CH_3CN)_2$, $PdBr_2(CH_3CN)_2$, $PdI_2(CH_3CN)_2$, $PdCl_2(C_6H_5CN)_2$, $PdBr_2(C_6H_5CN)_2$, $PdI_2(C_6H_5CN)_2$, $PdCl_2(cod)$, $PdBr_2(cod)$, $PdI_2(cod)$, $PdCl_2(nbd)$, $PdBr_2(nbd)$, $PdI_2(nbd)$, $Pd(OAc)_2$, and $Pd(acac)_2$.

Palladium complexes are prepared by, for example, allowing L and π-allylpalladium chloride ($[(\pi\text{-allyl})PdCl]_2$) to react in accordance with the method disclosed in the literature (Y. Uozumi and T. Hayashi, J. Am. Chem. Soc., vol. 113, p. 9887 (1991)). Specific examples of the oligomeric or polymeric palladium complexes are $(PdCl_2)_k(L)$, $[(\pi\text{-allyl})Pd]_k(L)$, $[Pd_k(L)](ClO_4)_k$, $[Pd_k(L)](PF6)_k$, and $[Pd_k(L)](BF_4)_k$.

Iridium Complexes:

Iridium compounds used as an iridium complex precursor include $IrCl_3$, $IrBr_3$, $IrI_3$, $[Ir(cod)Cl]_2$, $[Ir(cod)Br]_2$, $[Ir(cod)I]_2$, $[Ir(nbd)Cl]_2$, $[Ir(nbd)Br]_2$, $[Ir(nbd)I]_2$, $[Ir(cod)(OAc)]_2$, $[Ir(nbd)(OAc)]_2$, $Ir(cod)(acac)$, $Ir(nbd)(acac)$, $Ir(CO)_2(acac)$, $[Ir(CO)_2Cl]_2$, $[Ir(CO)_2Br]_2$, $[Ir(CO)_2I]_2$, $[Ir(cod)_2]BF_4$, $[Ir(cod)_2]ClO_4$, $[Ir(cod)_2]PF_6$, $[Ir(cod)_2]BPh_4$, $[Ir(nbd)_2]BF_4$, $[Ir(nbd)_2]ClO_4$, $[Ir(nbd)_2]PF_6$, and $[Ir(nbd)_2]BPh_4$.

The iridium complexes are prepared by, for example, stirring L and [(1,5-cyclooctadiene)(acetonitrile)iridium] tetrafluoroborate ($[Ir(cod)(CH_3CN)_2]BF_4$) in tetrahydrofuran in accordance with the method disclosed in the literature (K. Mashima, et al., J. Organomet. Chem., vol. 428, p. 213 (1992)). Specific examples of the oligomeric or polymeric iridium complexes include $[Ir_k(cod)_k(L)](ClO_4)_k$, $[Ir_k(cod)_k(L)](PF_6)_k$, $[Ir_k(cod)_k(L)](BF_4)_k$, $[Ir_k(nbd)_k(L)](ClO_4)_k$, $[Ir_k(nbd)_k(L)](PF_6)_k$, $[Ir_k(nbd)_k(L)](BF_4)_k$, $Ir_k(cod)_k(L)Cl_k$, $Ir_k(nbd)_k(L)Cl_k$, $Ir_k(cod)_k(L)Br_k$, and $Ir_k(nbd)_k(L)Br_k$.

The oligomeric or polymeric transition metal complex having the structural unit (VI) is preferably prepared by polymerizing the transition metal complex (II) or allowing a polymer having the structural unit (III) obtained by polymerizing the phosphine derivative (I) to react with a transition metal compound. The polymeric transition metal complex having the structural units (VI), (IV), and (V) is preferably prepared by copolymerizing the transition metal complex (II), the styrene derivative (IVa), and the divinylbenzene (Va) or allowing a copolymer having the structural units (III), (IV), and (V) obtained by copolymerizing the phosphine derivative (I), the styrene derivative (IVa), and the divinylbenzene (Va) to react with a transition metal compound.

The polymerization reaction is carried out by solution polymerization, suspension polymerization and the like. For example, a solution or suspension of the monomer(s) in a solvent, such as a polyvinyl alcohol aqueous solution, a halogenated hydrocarbon (e.g., chloroform) or a hydrocarbon (e.g., toluene), is charged in a reaction vessel in an inert atmosphere (e.g., nitrogen or argon). An azo compound (e.g., 2,2'-azobis(2,4-dimethylvaleronitrile) or azobisisobutyronitrile) or a peroxide is added as a radical polymerization initiator, and the mixture was allowed to react at 60 to 100° C. under atmospheric pressure for 1 hour to 2 days.

The copolymerization ratio of the units (VI), (IV), and (V), represented by the molar ratio k:l:m, is 2 to 100:0 to 1000:0 to 1000, preferably 2 to 100:100 to 1000:0 to 1000. The degrees of polymerization of the units (VI), (IV), and (V) are represented by k, l, and m, respectively, and (k+l+m) is in the range of from 10 to 1000.

The oligomeric or polymeric transition metal complex having the structural unit (VI) and the polymeric transition metal complex having the structural units (VI) and (IV) and/or (V) are useful as a catalyst for asymmetrical synthesis. For example, they catalyze asymmetrical hydrogenation of an olefin compound (A) to obtain an optically active amino acid compound (B):

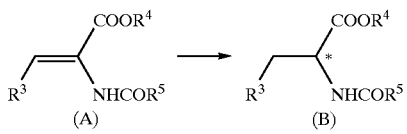

wherein $R^3$ represents a substituted or unsubstituted alkyl group or a substituted or unsubstituted aryl group; $R^4$ represents a hydrogen atom, an alkyl group, a substituted or unsubstituted aryl group or a substituted or unsubstituted aralkyl group; $R^5$ represents a hydrogen atom, an alkyl group, an alkoxy group, a substituted or unsubstituted aryl group or a substituted or unsubstituted aralkyloxy group; and * indicates an asymmetric carbon atom.

That is, an optically active amino acid compound (B) having a desired absolute configuration can be synthesized by the above reaction being carried out in the presence of a transition metal complex having, as a ligand, either the (R)-form or the (S)-form of the phosphine derivative (I) or of the oligomer or polymer (III) as a catalyst.

In formulae (A) and (B), the alkyl group as $R^3$ includes an alkyl group having 1 to 8 carbon atoms, such as methyl, ethyl, propyl, isopropyl, n-butyl, t-butyl, pentyl, hexyl, heptyl and octyl, which may be substituted with a halogen atom, an alkoxy group, etc. The aryl group as $R^3$, $R^4$ or $R^5$ includes an aryl group having 6 to 14 carbon atoms, such as phenyl or naphthyl, which may be substituted with a lower alkyl group having 1 to 4 carbon atoms (e.g., methyl, ethyl, propyl, isopropyl, n-butyl, t-butyl, isobutyl), a halogen atom (e.g., fluorine, chlorine, bromine), a lower alkoxy group having 1 to 4 carbon atoms (e.g., methoxy, ethoxy, propoxy, butoxy), a halogenated lower alkyl group (e.g., trifluoromethyl, trichloromethy), a benzyloxy group, etc. The substituted or unsubstituted aryl group preferably includes phenyl, 2-, 3- or 4-methoxyphenyl, 2-, 3- or 4-chlorophenyl, 2-, 3- or 4-fluorophenyl, 2-, 3- or 4-trifluoromethylphenyl, and 2-, 3- or 4-tolyl.

The aralkyl group as represented by $R^4$ preferably includes a substituted or unsubstituted aralkyl group having 7 to 11 carbon atoms, particularly a benzyl group which may be substituted. The aralkyloxy group as $R^5$ preferably includes a substituted or unsubstituted aralkyloxy group having 7 to 11 carbon atoms, particularly a benzyloxy group which may be substituted. Substituents of the aralkyl group and the aralkyloxy group include a lower alkyl group having 1 to 4 carbon atoms (e.g., methyl, ethyl, propyl, isopropyl, n-butyl, t-butyl, isobutyl), a halogen atom (e.g., fluorine, chlorine, bromine), a lower alkoxy group having 1 to 4 carbon atoms (e.g., methoxy, ethoxy, propoxy, butoxy), a halogenated lower alkyl group (e.g., trifluoromethyl, trichloromethyl), and a benzyloxy group.

The alkyl group as $R^4$ or $R^5$ preferably includes a lower alkyl group, particularly an alkyl group having 1 to 4 carbon atoms, such as methyl, ethyl, propyl, isopropyl, butyl, t-butyl, and isobutyl groups.

The alkoxy group as $R^5$ preferably includes a lower alkoxy group, particularly an alkoxy group having 1 to 4 carbon atoms, such as methoxy, ethoxy, propoxy, isopropoxy, butoxy, and t-butoxy groups.

Any solvents that do not hinder the reaction can be used. Useful solvents include alcohols, such as methanol, ethanol, propanol, isopropyl alcohol, butanol, and benzyl alcohol; aromatic hydrocarbons, such as benzene, toluene, and xylene; ethers, such as diethyl ether, diisopropyl ether, dioxane, dioxolane, and tetrahydrofuran; halogenated hydrocarbons, such as methylene chloride, chloroform, 1,2-dichloroethane, 1,1,2,2-tetrachloroethane; esters, such as ethyl acetate; nitriles, such as acetonitrile; and amides, such as N,N-dimethylformamide. These solvents can be used either individually or as a mixture of two or more thereof in an appropriate mixing ratio. The solvent is usually used in an amount of 1 to 1,000 parts by volume, preferably 2 to 500 parts by volume, still preferably 2 to 20 parts by volume, per part by weight of compound (A).

The complex catalyst is preferably used in an amount of about 0.01 to 10 mo %, particularly 0.05 to 5 mol%, in terms of the transition metal complex (II) or the oligomeric or polymeric transition metal complex having the unit (VI) or the polymeric transition metal complex having the units (VI) and (IV) and/or (V) based on the reaction substrate.

The reaction is usually carried out at about 10 to 100° C., preferably about 20 to 50° C., under a hydrogen pressure of about 2 to 120 atm. for about 10 minutes to 30 hours. These reaction conditions are subject to variation depending on the amount of the reactant used, and the like.

After the reaction, the oligomeric or polymeric transition metal complex comprising the unit (VI) or the units (VI) and (IV) and/or (V) can be separated practically completely from the reaction product through simple means, such as centrifugation or filtration. The catalyst thus recovered can be reused.

The invention will now be illustrated in greater detail with reference to Examples, but it should be understood that the invention is not construed as being limited thereto and that various changes and modifications can be made therein without departing from the spirit and scope of the invention.

In Examples, measurements of physical properties were made with the following apparatus.

$^1$H-NMR: JMN-EX-270 (270 MHz), made by JEOL, Ltd.
$^{31}$P-NMR: JMN-EX-270 (109 MHz), made by JEOL, Ltd.
Specific rotation: DIP-360, made by JASCO, Inc. GLC: GC-15A, made by Shimadzu Corp. Mass: QP-1000, made by Shimadzu Corp.

EXAMPLE 1

Synthesis of (R)-6-Vinyl-2,2'-bis (diphenylphosphino)-1,1'-binaphthalene (1) Synthesis of (R)-2,2'-bis(Trifluoromethanesulfonyloxy)-1,1'-binaphthalene In 181 ml of methylene chloride were dissolved 36.2 g (127 mmol) of (R)-binaphthol and 25.2 g (319 mmol) of pyridine, and the solution was cooled to 0° C. To the solution was added dropwise 76.5 ml (271 mmol) of trifluoromethanesulfonic acid anhydride, followed by stirring at room temperature for 18 hours. The reaction mixture was washed with 200 ml of 2N hydrochloric acid. The organic layer was washed successively with water and a sodium chloride aqueous solution. The solvent was evaporated to give 69.3 g of a crude product. Recrystallization from 280 ml of hexane yielded 64.1 g (92%) of the title compound.

$^1$H-NMR (CDCl$_3$) δ: 7.25–8.15 (m, aromatic).

(2) Synthesis of (R)-2'-Diphenylphosphinyl-2-(trifluoromethanesulfonyloxy)-1,1'-binaphthalene In 100 ml of dimethyl sulfoxide were dissolved 11 g (20 mmol) of (R)-2,2'-bis(trifluoromethanesulfonyloxy)-1,1'-binaphthalene, 0.225 g (50 mol%) of palladium acetate, and 0.43 g (50 mol%) of 1,3-bis(diphenylphosphino)propane, and the mixture was stirred at room temperature for 1.5 hours. A solution of 8.08 g (40 mmol) of diphenylphosphine oxide and 20 ml of diisopropylethylamine in 100 ml of dimethyl sulfoxide was added thereto, followed by stirring at 100° C. for 12 hours. The reaction mixture was cooled to room temperature, and 75 ml of methylene chloride was added thereto. The solution was cooled in an ice bath, and 100 ml of 2N hydrochloric acid was slowly dropped therein, followed by stirring at room temperature for 30 minutes. After liquid-liquid separation, the aqueous layer was extracted with methylene chloride. The combined organic layer was washed with water, dried over anhydrous magnesium sulfate, followed by concentration. The residue was purified by silica gel column chromatography (hexane/ethyl acetate=4:1 to 1:4) to afford 11.5 g (96%) of the title compound as yellowish white crystals.

[α]$^4$: +44.45° (c=0.50, CHCl$_3$); $^1$H-NMR (CDCl$_3$) δ: 7.0–8.01 (m, aromatic); $^{31}$P-NMR (CDCl$_3$) δ: 28.73 (s).

(3) Synthesis of (R)-2'-Diphenylphosphinyl-2-hydroxy-1,1'-binaphthalene

A mixture of 11.5 g (19.2 mmol) of (R)-2'-diphenylphosphinyl-2-trifluoromethanesulfonyloxy-1,1'-binaphthalene, 2.42 g (57.6 mmol) of lithium hydroxide monohydrate, 75 ml of tetrahydrofuran, and 25 ml of purified water was stirred overnight. Tetrahydrofuran was removed by evaporation under reduced pressure, 30 ml of toluene and 50 ml of 2N hydrochloric acid were added to the residue, and the mixture was stirred, followed by liquid-liquid separation. The organic layer was dried over anhydrous magnesium sulfate, and the solvent was evaporated to give 9.03 g (100%) of the title compound.

(4) Synthesis of (R)-6-Bromo-2'-diphenylphosphinyl-2-hydroxy-1,1'-binaphthalene

In 150 ml of dioxane was dissolved 4 g (8.49 mmol) of (R)-2'-diphenylphosphinyl-2-hydroxy-1,1'-binaphthalene, and a solution of 1.75 ml (34 mmol) of bromine in 20 ml of dioxane was added to the solution dropwise at 5° C. After stirring at room temperature for 2 hours, the reaction mixture was neutralized with an aqueous solution of sodium thiosulfate and extracted with chloroform. The organic layer was washed with a saturated aqueous solution of sodium chloride and dried over anhydrous magnesium sulfate. The solvent was evaporated under reduced pressure, and the resulting yellow solid was purified by silica gel column chromatography (methylene chloride/ethyl acetate=1/1) to furnish 4.06 g (87%) of the title compound.

$^1$H-NMR (CDCl$_3$) δ: 9.05 (bs, 1H), 7.95–7.17 (m, 2H), 7.65–7.53 (m, 7H), 7.42–7.32 (m, 2H), 7.26–7.17 (m, 2H), 7.06–6.88 (m, 3H), 6.81–6.72 (m, 2H), 6.27 (d, J=8.91 Hz, 1H); $^{31}$P-NMR (CDCl$_3$) δ: 31.26(s).

(5) Synthesis of (R)-6-Bromo-2'-diphenylphosphino-2-hydroxy-1,1'-binaphthalene

In 40 ml of xylene was dissolved 3.09 g (5.63 mmol) of (R)-6-bromo-2'-diphenylphosphinyl-2-hydroxy-1,1'-binaphthalene, and 15.7 ml (112 mmol) of triethylamine was added to the solution. To the solution was further added 5.7 ml (56.4 mmol) of trichlorosilane, followed by stirring at 110° C. for 22 hours. A saturated sodium hydrogencarbonate aqueous solution was added to cease the reaction. The salt was separated by filtration, and the filtrate was washed with toluene. The organic layer separated by liquid-liquid separation was dried over anhydrous magnesium sulfate, and the solvent was evaporated. The residue was purified by silica gel column chromatography (chloroform) to give 1.94 g (65%) of the title compound.

$^1$H-NMR (CDCl$_3$) δ: 7.96–7.80 (m, 4H), 7.52–7.43 (m, 2H), 7.33–6.98 (m, 14H), 6.55 (d, J=8.91 Hz, 1H), 4.62 (s, 1H); $^{31}$P-NMR (CDCl$_3$) δ: –12.82 (s).

(6) Synthesis of (R)-6-Vinyl-2'-diphenylphosphino-2-hydroxy-1,1'-binaphthalene

In 12 ml of dimethylformamide were dissolved 1.0 g (1.88 mmol) of (R)-6-bromo-2'-diphenylphosphinyl-2-hydroxy-1,1'-binaphthalene, 10 mg (0.182 mmol) of tetrakis(triphenylphosphine)palladium (Pd(PPh$_3$)$_4$), 0.4 ml (2.87 mmol) of 2-vinyl-5,5-dimethyl-1,3,2-dioxaborinane, and 0.965 g (4.54 mmol) of potassium tertiary phosphate monohydrate and stirred at 80° C. for 16 hours. The reaction mixture was diluted with water and extracted with diethyl ether. The organic. layer was washed with a saturated aqueous solution of sodium chloride and dried over anhydrous magnesium sulfate. The solvent was evaporated, and the residue was purified by silica gel column chromatography (chloroform) to afford 618 mg (68%) of the title compound.

$^1$H-NMR (CDCl$_3$) δ: 7.95–7.86 (m, 3H), 7.72 (bs, 1H), 7.54–7.01 (m, 16H), 6.79 (dd, J=17.15, 10.55 Hz, 1H), 6.69 (d, J=8.91 Hz, 1H), 5.70 (d, J=17.15 Hz, 1H), 5.22 (d, J=10.55 Hz, 1H), 4.53 (s, 1H); $^{31}$P-NMR (CDCl$_3$) δ: –13.01 (s).

(7) Synthesis of (R)-6-Vinyl-2'-diphenylphosphino-2-trifluoromethanesulfonyloxy-1,1'-binaphthalene 60% Sodium hydride (434.3 mg, 10.9 mmol) was washed with hexane, and 4.00 g (8.32 mmol) of (R)-6-vinyl-2'-diphenylphosphino-2-hydroxy-1,1'-binaphthalene and 70 ml of tetrahydrofuran were added thereto, followed by stirring for 1 hour. To he mixture was added 1.55 ml (10.4 mmol) of trifluoromethanesulfonic acid anhydride at –78° C., and the mixture was stirred at that temperature for 1 hour. A sodium hydrogencarbonate aqueous solution was added to stop the reaction, and the reaction mixture was extracted with toluene. The organic layer was washed with a saturated sodium chloride aqueous solution and dried over anhydrous magnesium sulfate. The solvent was evaporated, and the residue was purified by silica gel column chromatography (hexane/methyl chloride=1/1) to give 3.48 g (68%) of the title compound.

$^1$H-NMR (CDCl$_3$) δ: 8.04–7.82 (m, 4H), 7.54–7.42 (m, 3H), 7.33–6.77 (m, 15H), 5.79 (d, J=17.49 Hz, 1H), 5.35 (d, J=10.89 Hz, 1H); $^{31}$P-NMR (CDCl$_3$) δ: –12.51 (s).

(8) Synthesis of (R)-6-Vinyl-2'-diphenylphosphino-2-diphenylphosphinyl-1,1'-binaphthalene In 4 ml of dimethylformamide were dissolved 366.6 mg (0.597 mmol) of (R)-6-vinyl-2'-diphenylphosphino-2-trifluoromethanesulfonyloxy-1,1'-binaphthalene, 167.0 mg (0.826 mmol) of diphenylphosphine oxide, 29.0 mg (5.49× 10$^{-5}$ mmol) of dichloro[2-(diphenylphosphino)ethyl]nickel (NiCl$_2$(dppe)), and 125.0 mg (1.11 mmol) of 1,4-diazabicyclo[2,2,2,]octane, and the solution was stirred at 90° C. for 28 hours. After allowing the reaction mixture to cool to room temperature, water and methylene chloride were added, followed by liquid-liquid separation. The organic layer was washed with a saturated sodium chloride aqueous solution and dried over anhydrous magnesium sulfate. The solvent was evaporated, and the residue was purified by silica gel column chromatography (methylene chloride/ethyl acetate=1:0 to 4:1) to yield 227.7 mg (57%) of the title compound.

$^1$H-NMR (CDCl$_3$) δ: 7 90–7.54 (m, 5H), 7.41–6.70 (m, 26H), 6.49 (d, J=9.2 Hz, 1H), 5.69 (d, J=17.48 Hz, 1H), 5.29 (d, J=11.32 Hz, 1H); $^{31}$P-NMR (CDCl$_3$) δ: 27.94 (s), −14.34 (s).

(9) Synthesis of (R)-6-Vinyl-2,2'-bis(diphenylphosphino)-1,1'-binaphthalene

To 30 ml of xylene were added 1.66 g (2.50 mmol) of (R)-6-vinyl-2'-diphenylphosphino-2-diphenylphosphinyl-1,1'-binaphthalene, 3.2 ml (25.2 mmol) of N,N-dimethylaniline, and 2.5 ml (24.7 mmol) of trichlorosilane, and the mixture was stirred at 90° C. for 18 hours. The reaction mixture was cooled to 0° C., and 1N aqueous sodium hydroxide was added thereto slowly. The aqueous layer was separated and extracted with toluene. The organic layer was washed successively with 1N hydrochloric acid and a saturated sodium chloride aqueous solution, and dried over anhydrous magnesium sulfate. The solvent was evaporated, and the residue was purified by silica gel column chromatography (methylene chloride) to furnish 1.65 g (100%) of the title compound.

$^1$H-NMR (CDCl$_3$) δ: 7.89–7.72 (m, 4H), 7.45–6.71 (m, 28H), 5.72 (d, J=17.48 Hz, 1H), 5.27 (d, J=11.55 Hz, 1H), 5.29 (d, J=11.32 Hz, 1H); $^{31}$P-NMR (CDCl$_3$) δ: −14.8 (d, J=10–7 Hz), −14.9 (d, J=10.7 Hz).

EXAMPLE 2

(1) Suspension Copolymerization

A 0.4% aqueous solution of polyvinyl alcohol was stirred well. A toluene (0.75 ml) solution of 100 mg (0.126 mmol) of (R)-6-vinyl-2,2'-bis(diphenylphosphino)-1,1'-binaphthalene, 0.45 ml (3.93 mmol) of styrene, 0.035 ml (0.135 mmol) of divinylbenzene, and 20.2 mg (0.0813 mmol) of 2,2'-azobis(2,4-dimethylvaleronitrile) (hereinafter referred to as V-65) was added to the polyvinyl alcohol solution at 80° C. The reaction mixture was stirred at a speed of 400 rpm for 24 hours. The resulting polymer was collected by filtration, washed with water and then with methanol, and dried under reduced pressure to obtain a yellowish white solid (310 mg).

(2) Solution Copolymerization in Chloroform

In a 20 ml Shlenk tube were put 100 mg (0.126 mmol) of (R)-6-vinyl-2,2'-bis(diphenylphosphino)-1,1'-binaphthalene, 0.42 ml (3.66 mmol) of styrene, 0.11 ml (0.424 mmol) of divinylbenzene, 20.1 mg (0.081 mmol) of V-65, and 1.5 ml of chloroform, and the mixture was heated at 70° C. for 5 hours. Methanol was added to the solidified reaction mixture, whereby a white precipitate was formed, which was collected by filtration, washed successively with methanol and toluene, and dried under reduced pressure to give a yellowish white solid (587 mg).

(3) Solution Copolymerization in Toluene

In a 20 ml Shlenk tube were put 100 mg (0.126 mmol) of (R)-6-vinyl-2,2'-bis(diphenylphosphino)-1,1'-binaphthalene, 0.42 ml (3.66 mmol) of styrene, 0.11 ml (0.424 mmol) of divinylbenzene, 20.1 mg (0.081 mmol) of V-65, and 1.5 ml of toluene, and the mixture was heated at 70° C. for 5 hours. Methanol was added to the solidified reaction mixture to form a white precipitate, which was collected by filtration, washed successively with methanol and toluene, and dried under reduced pressure to give a yellowish white solid (114 mg).

(4) Solution Copolymerization in Toluene

In a 20 ml Shlenk tube were put 50 mg (7.77×10$^{-2}$ mmol) of (R)-6-vinyl-2,2'-bis(diphenylphosphino)-1,1'-binaphthalene, 0.285 ml (2.48 mmol) of styrene, 19.31 mg (0.077 mmol) of V-65, and 1.5 ml of toluene, and the mixture was heated at 80° C. for 16 hours. Methanol was added to the solidified reaction mixture to form a white precipitate, which was collected by filtration, washed with methanol, and dried under reduced pressure to give a yellowish white solid (300 mg).

EXAMPLE 3

Reaction Between Polymer and Dicarbonylacetylacetonatorhodium

In a 20 ml Shlenk tube were put 11 mg (2.71×10$^{-2}$ mmol) of di(1,5-cyclooctadiene)rhodium tetrafluoroborate ([Rh(cod)$_2$]BF$_4$) 215 mg (corresponding to 5.40×10$^2$ mmol of the monomer) of the polymer obtained in Example 2-(4), and 4 ml of methylene chloride, and the mixture was stirred at room temperature for 14 hours. The reaction mixture was dried under reduced pressure to give a yellowish orange solid (214 mg).

EXAMPLE 4

Synthesis of (1,5-Cyclooctadiene)((R)-6-vinyl-2,2'-bis(diphenylphosphino)-1,1'-binaphthalene)rhodium tetrafluoroborate In a 20 ml Shlenk tube were put 11 mg (2.71×10$^{-2}$ mmol) of di(1,5-cyclooctadiene)rhodium tetrafluoroborate ([Rh(cod)$_2$]BF$_4$), 17.6 mg (2.71×10$^{-2}$ mmol) of (R)-6-vinyl-2,2'-bis (diphenylphosphino)-1,1'-binaphthalene obtained in Example 1, and 4 ml of methylene chloride, and the mixture was stirred at room temperature for 14 hours. The reaction mixture was dried under reduced pressure to afford the title compound as a yellowish orange powder (25 mg).

$^1$H-NMR (CDCl$_3$) δ: 7.89–7.72 (m, 4H), 7.45–6.71 (m, 28H), 5.72 (d, J=17.48 Hz, 1H), 5.27 (d, J=11.55 Hz, 1H), 5.29 (d, J=11.32 Hz, 1H); $^{31}$P-NMR (CDCl$_3$) δ: −14.8 (d, J=10.7 Hz), −14.9 (d, J=10.7 Hz).

EXAMPLE 5

(1) Suspension Copolymerization

A 0.4% aqueous solution of polyvinyl alcohol was stirred well. A toluene (0.75 ml) solution of 100 mg (0.126 mmol) of (1,5-cyclooctadiene)((R)-6-vinyl-2,2'-bis(diphenylphosphino)-1,1-binaphthalene)rhodium tetrafluoroborate obtained in Example 4, 0.45 ml (3.93 mmol) of styrene, 0.035 ml (0.135 mmol) of divinylbenzene, and 20.2 mg (0.0813 mmol) of V-65 was added to the polyvinyl alcohol solution at 80° C. The reaction mixture was stirred at a speed of 400 rpm for 24 hours. The resulting polymer was collected by filtration, washed with water and then with methanol, and dried under reduced pressure to obtain a yellowish orange solid (520 mg).

(2) Solution Copolymerization in Chloroform

In a 20 ml Shlenk tube were put 100 mg (0.126 mmol) of (1,5-cyclooctadiene)((R)-6-vinyl-2,2'-bis(diphenylphosphino)-1,1'-binaphthalene)rhodium tetrafluoroborate obtained in Example 4, 0.42 ml (3.66 mmol) of styrene, 0.11 ml (0.424 mmol) of divinylbenzene, 20.1 mg (0.081 mmol) of V-65, and 1.5 ml of chloroform, and the mixture was heated at 70° C. for 5 hours. Methanol was added to the solidified reaction mixture to form a white precipitate, which was collected by filtration, washed successively with methanol and toluene, and dried under reduced pressure to give a yellowish orange solid (560 mg).

(3) Solution Copolymerization in Toluene

In a 20 ml Shlenk tube were put 100 mg (0.126 mmol) of (1,5-cyclooctadiene)((R)-6-vinyl-2,2'-bis (diphenylphosphino)-1,1'-binaphthalene)rhodium tetrafluoroborate obtained in Example 4, 0.42 ml (3–66 mmol) of styrene, 0.11 mg (0.424 mmol) of divinylbenzene, 20.1 mg (0.081 mmol) of V-65, and 1.5 ml of toluene, and the mixture was heated at 70° C. for 5 hours. Methanol was added to the solidified reaction mixture to form a white precipitate, which was collected by filtration, washed successively with methanol and toluene, and dried under reduced pressure to give a yellowish orange solid (560 mg).

(4) Solution Copolymerization in Toluene

In a 20 ml Shlenk tube were put 50 mg ($7.77\times10^{-2}$ mmol) of (1,5-cyclooctadiene)((R)-6-vinyl-2,2'-bis (diphenylphosphino)-1,1'-binaphthalene)rhodium tetrafluoroborate obtained in Example 4, 0.285 ml (2.48 mmol) of styrene, 19.31 mg (0.077 mmol) of V-65, and 1.5 ml of toluene, and the mixture was heated at 80° C. for 16 hours. Methanol was added to the solidified reaction mixture to form a white precipitate, which was collected by filtration, washed with methanol, and dried under reduced pressure to give a yellowish white solid (290 mg).

EXAMPLE 6

In a 100 ml stainless steel autoclave were put 15 mg of the ruthenium complex synthesized in Example 3 (containing $2.5\times10^{-2}$ mmol of Rh), 700 mg (2.5 mmol) of methyl(Z)-α-benzamidocinnamate and 7.5 ml of tetrahydrofuran, and the mixture was stirred at room temperature under a hydrogen pressure of 3 atm. for 24 hours. The reaction mixture was withdrawn and filtered to remove the catalyst. The conversion was found to be 88% by $^1$H-NMR analysis. The optical purity was 57%e.e. as measured by HPLC using a chiral column (Chiralcel OJ; 1.0 ml/min; 2-propanol/hexane=1:9).

EXAMPLE 7

Reuse of Catalyst:

In a 50 ml glass pressure bottle were put 15 mg of the rhodium complex synthesized in Example 3 (containing $2.5\times10^{-2}$ mmol of Rh), 700 mg (2.5 mmol) of methyl(Z)-α-benzamidocinnamate, and 7.5 ml of tetrahydrofuran, and the mixture was stirred at room temperature under a hydrogen pressure of 3 atm. for 3 hours. The conversion was 92%, and the optical purity was 56%e.e.

After the reaction, the supernatant liquid of the benzene solution containing the reaction product and the substrate was taken out with a syringe in an argon atmosphere. The solid phase was washed with benzene. To the thus recovered catalyst were added 700 mg (2.5 mmol) of methyl(Z)-α-benzamidocinnamate and 7.5 ml of tetrahydrofuran, and the catalytic reaction was carried out in the same manner as described above. The conversion was 85%, and the optical yield was 54%e.e.

The polymer-bearing phosphine ligand of the invention is an excellent ligand for asymmetric synthesis. A rhodium, ruthenium or like transition metal complex of the polymeric phosphine ligand exhibits excellent catalyst performance, such as catalytic activity, in asymmetric hydrogenation. Because the complex is insoluble in most solvents, it can easily be separated from the reaction product by filtration. Therefore, the complex is a superior catalyst for industrial use.

What is claimed is:

1. An oligomer or polymer having a structural unit represented by formula (III):

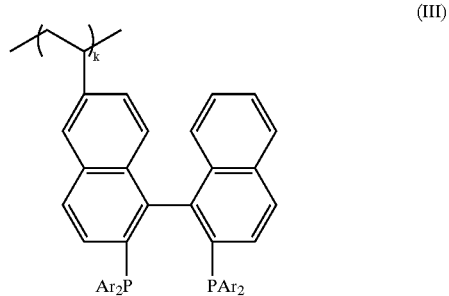

(III)

wherein Ar represents a substituted or unsubstituted phenyl group or a substituted or unsubstituted naphthyl group, and k represents an integer of 2 to 100.

2. A copolymer having a structural unit represented by formula (III) and a structural unit represented by formula (IV) and/or a structural unit represented by formula (V):

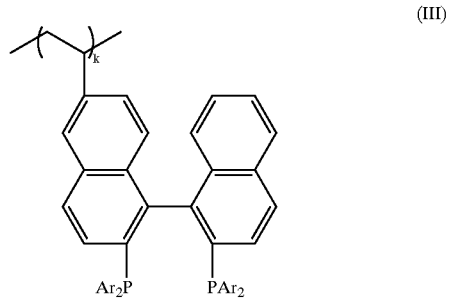

(III)

(IV)

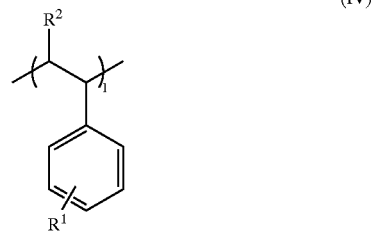

(V)

wherein Ar represents a substituted or unsubstituted phenyl group or a substituted or unsubstituted naphthyl group; $R^1$ represents a hydrogen atom, a lower alkyl group, a lower alkoxy group or a halogen atom; $R^2$ represents a hydrogen atom or a methyl group; k represents an integer of 2 to 100; and l and m each represent an integer of 0 to 1000 provided that l and m do not simultaneously represent 0 and that the sum of k, l, and m ranges from 10 to 1000.

3. A transition metal complex obtained by allowing a transition metal compound to react with the oligomer or polymer according to claim 1 or the copolymer according to claim 2.

4. A transition metal complex according to claim 3, which has a structural unit represented by formula (VI):

(VI)

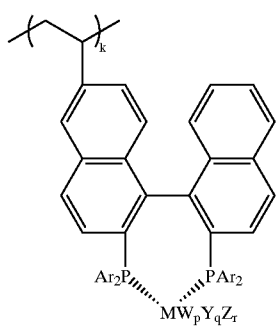

wherein Ar and k are as defined in claim 1 or 2; M represents ruthenium, rhodium, iridium or palladium; W represents an allyl group, a methallyl group, 1,5-cyclooctadiene, norbornadiene, a halogen atom, an acetoxy group or an acetylacetonato group; Y represents a hydrogen atom, a halogen atom, $ClO_4$, $BF_4$, $PF_6$, $BPh_4$ (tetraphenylborate), OTf (trifluoromethanesulfonyloxy) or $SbF_6$; Z represents a substituted or unsubstituted benzene; and p, q, and r each represent a number of 0 to 2 provided that p, q, and r do not simultaneously represent 0.

5. A transition metal complex according to claim 3, which has a structural unit represented by formula (VI) and a structural unit represented by formula (IV) and/or a structural unit represented by formula (V):

(VI)

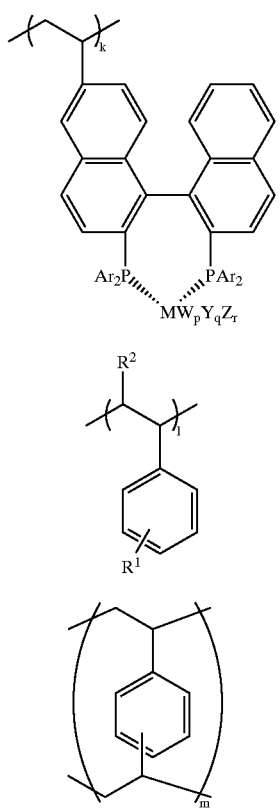

(IV)

(V)

wherein Ar, $R^1$, $R^2$, k, l, and m are as defined in claim 1 or 2; M represents ruthenium, rhodium, iridium or palladium; W represents an allyl group, a methallyl group, 1,5-cyclooctadiene, norbornadiene, a halogen atom, an acetoxy group or an acetylacetonato group; Y represents a hydrogen atom, a halogen atom, $ClO_4$, $BF_4$, $PF_6$, $BPh_4$ (tetraphenylborate), OTf (trifluoromethanesulfonyloxy) or $SbF_6$; Z represents a substituted or unsubstituted benzene; and p, q, and r each represent a number of 0 to 2 provided that p, q, and r do not simultaneously represent 0.

6. A process for producing an oligomer or polymer having a structural unit represented by formula (III):

(III)

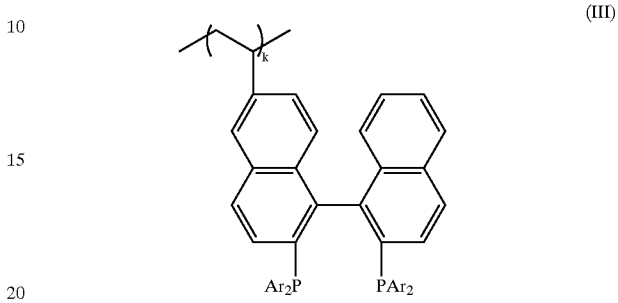

wherein Ar represents a substituted or unsubstituted phenyl group or a substituted or unsubstituted naphthyl group; and k represents an integer of 2 to 100, comprising solution polymerization or suspension polymerization of a phosphine derivative represented by formula (I):

(I)

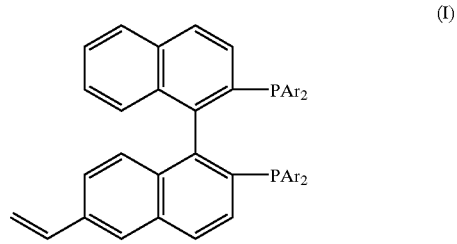

wherein Ar is as defined above.

7. A process for producing a copolymer having a structural unit represented by formula (III) and a structural unit represented by formula (IV) and/or a structural unit represented by formula (V):

(III)

(IV)

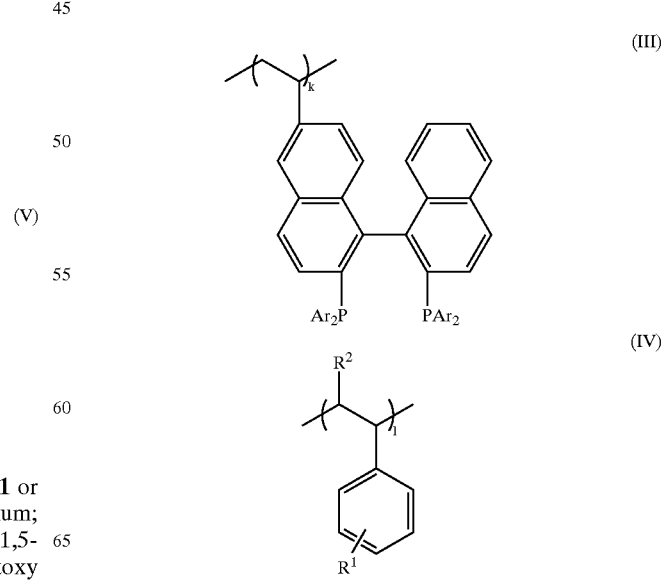

(V)

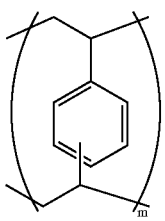

wherein Ar represents a substituted or unsubstituted phenyl group or a substituted or unsubstituted naphthyl group; $R^1$ represents a hydrogen atom, a lower alkyl group, a lower alkoxy group or a halogen atom; $R^2$ represents a hydrogen atom or a methyl group; k represents an integer of 2 to 100; and l and m each represent an integer of 0 to 1000 provided that l and m do not simultaneously represent 0 and that the sum of k, l, and m ranges from 10 to 1000, comprising solution copolymerization or suspension copolymerization of a phosphine derivative represented by formula (I):

(I)

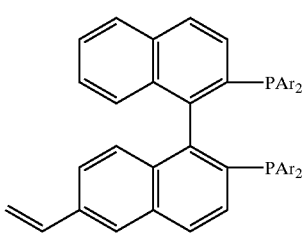

wherein Ar is as defined above, with a styrene derivative represented by formula (IVa):

(IVa)

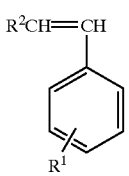

wherein $R^1$ and $R^2$ are as defined above, and/or divinylbenzene represented by formula (Va):

(Va)

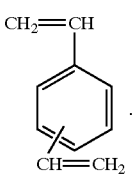

8. A process for producing a transition metal complex having a structural unit represented by formula (VI):

(VI)

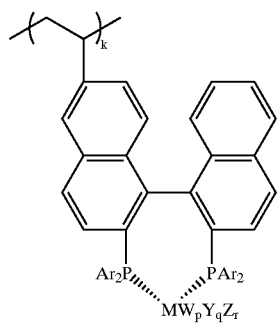

wherein Ar represents a substituted or unsubstituted phenyl group or a substituted or unsubstituted naphthyl group; M represents ruthenium, rhodium, iridium or palladium; W represents an allyl group, a methallyl group, 1,5-cyclooctadiene, norbornadiene, a halogen atom, an acetoxy group or an acetylacetonato group; Y represents a hydrogen atom, a halogen atom, $ClO_4$, $BF_4$, $PF_6$, $BPh_4$ (tetraphenylborate), OTf (trifluoromethanesulfonyloxy) or $SbF_6$; Z represents a substituted or unsubstituted benzene; k represents an integer of 2 to 100; and p, q, and r each represent a number of 0 to 2 provided that p, q, and r do not simultaneously represent 0, comprising solution polymerization or suspension polymerization of a transition metal complex represented by formula (II):

(II)

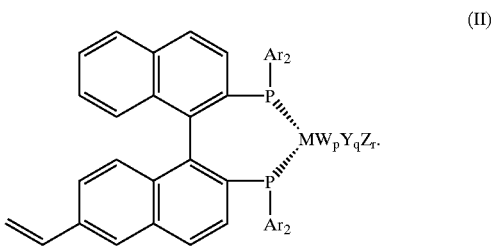

wherein Ar, M, W, Y, Z, p, q, and r are as defined above.

9. A process for producing a transition metal complex having a structural unit represented by formula (VI) and a structural unit represented by formula (IV) and/or a structural unit represented by formula (V):

(VI)

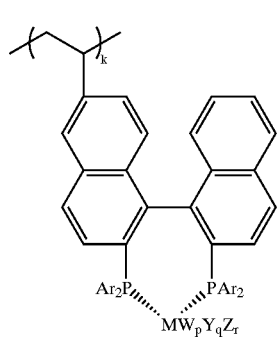

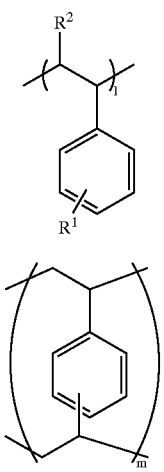

comprising solution copolymerization or suspension copolymerization of a transition metal complex represented by formula (II):

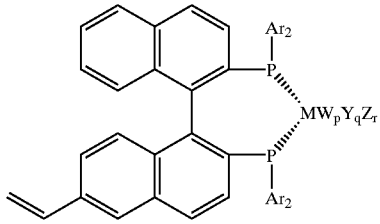

wherein Ar, M, W, Y, Z, p, q, and r are as defined above, with a styrene derivative represented by formula (IVa):

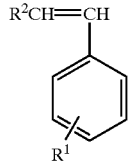

wherein $R^1$ and $R^2$ are as defined above, and/or divinylbenzene represented by formula (Va):

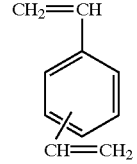

wherein Ar represents a substituted or unsubstituted phenyl group or a substituted or unsubstituted naphthyl group; $R^1$ represents a hydrogen atom, a lower alkyl group, a lower alkoxy group or a halogen atom; $R^2$ represents a hydrogen atom or a methyl group; M represents ruthenium, rhodium, iridiumorpalladium; W represents an allyl group, a methallyl group, 1,5-cyclooctadiene, norbornadiene, a halogen atom, an acetoxy group or an acetylacetonato group; Y represents a hydrogen atom, a halogen atom, $ClO_4$, $BF_4$, $PF_6$, $BPh_4$ (tetraphenylborate), OTf (trifluoromethanesulfonyloxy) or $SbF_6$; Z represents a substituted or unsubstituted benzene; p, q, and r each represent a number of 0 to 2 provided that p, q, and r do not simultaneously represent 0; k represents an integer of 2 to 100; and l and m each represent an integer of 0 to 1000 provided that l and m do not simultaneously represent 0 and that the sum of k, l, and m ranges from 10 to 1000,

* * * * *